(12) United States Patent
Sonveaux et al.

(10) Patent No.: US 10,799,470 B2
(45) Date of Patent: Oct. 13, 2020

(54) [$^{18}$F]-LABELLED LACTATE DERIVATIVE AS PET RADIOTRACER

(71) Applicant: GRANDIS, Woluwé-Saint-Lambert (BE)

(72) Inventors: Pierre Sonveaux, Sterrebeek (BE); Daniel Labar, Grand-Leez (BE); Vincent Van Hée, Braine-l'Alleud (BE); Gwenaël Dehon, Seneffe (BE); Raphaël Frédérick, Godinne (BE)

(73) Assignee: GRANDIS, Woluwé-Saint-Lambert (BE)

( * ) Notice: Subject to any disclaimer, the term of this patent is extended or adjusted under 35 U.S.C. 154(b) by 0 days.

(21) Appl. No.: 16/331,176

(22) PCT Filed: Sep. 8, 2017

(86) PCT No.: PCT/EP2017/072582
§ 371 (c)(1),
(2) Date: Mar. 7, 2019

(87) PCT Pub. No.: WO2018/046662
PCT Pub. Date: Mar. 15, 2018

(65) Prior Publication Data
US 2019/0255002 A1 Aug. 22, 2019

(30) Foreign Application Priority Data

Sep. 9, 2016 (EP) .................................... 16188093

(51) Int. Cl.
*A61K 31/19* (2006.01)
*A61B 6/03* (2006.01)
(Continued)

(52) U.S. Cl.
CPC .............. *A61K 31/19* (2013.01); *A61B 6/037* (2013.01); *A61B 6/5217* (2013.01); *C07B 59/001* (2013.01); *C07C 59/115* (2013.01)

(58) Field of Classification Search
CPC ...... A61B 6/037; A61B 6/5217; A61K 31/19; C07B 59/001; C07C 59/115
See application file for complete search history.

(56) References Cited

U.S. PATENT DOCUMENTS 4,149,012 A 4/1979 Dolling et al.

FOREIGN PATENT DOCUMENTS

| FR | 2290417 A1 | 6/1976 |
| WO | 03093412 A2 | 11/2003 |
| WO | 2010088564 A2 | 8/2010 |

OTHER PUBLICATIONS

Andrew P. Halestrap, "The SLC16 gene family—Structure, role and regulation in health and disease", Molecular Aspects of Medicine 34 (2013) 337-349, 13 pgs.
(Continued)

*Primary Examiner* — Valerie Rodriguez-Garcia
(74) *Attorney, Agent, or Firm* — Maier & Maier, PLLC

(57) ABSTRACT

A positron emission tomography (PET) radiotracer for imaging lactate uptake, wherein the tracer is a [$^{18}$F]-labelled lactate derivative which is [$^{18}$F]-3-fluoro-2-hydroxypropionic acid:

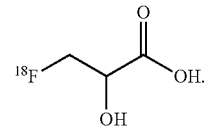

Also, a process for the radiosynthesis of the [$^{18}$F]-labelled lactate derivative. Further, the use of the [$^{18}$F]-labelled lactate derivative for imaging lactate uptake in living cells, especially in humans.

15 Claims, 6 Drawing Sheets

(51) Int. Cl.
*A61B 6/00* (2006.01)
*C07C 59/115* (2006.01)
*C07B 59/00* (2006.01)

(56) References Cited

OTHER PUBLICATIONS

Sheng-Feng Tsai et al., "Exercise Counteracts Aging-Related Memory Impairment: A Potential Role for the Astrocytic Metabolic Shuttle" Frontiers in Aging Neuroscience 2016, Mar. 2016, vol. 8, Article 57, 12 pgs.
Jhudit Pérez-Escuredo et al., "Monocarboxylate transporters in the brain and in cancer", Biochimica et Biophysica Acta (BBA)—Molecular Cell Research, vol. 1863, Issue 10, Oct. 2016, pp. 2481-2497, 17 pgs.
Christian Brinkmann et al., "Hyperlactatemia in type 2 diabetes: Can physical training help?", Journal of Diabetes and Its Complications 29 (2015) 965-969, 5 pgs.
L. Carneiro et al., "Monocarboxylate transporters: new players in body weight regulation", obesity reviews (2015) 16 (Suppl. 1), 55-86, 12 pgs.
Pierre Sonveaux et al., "Targeting lactate-fueled respiration selectively kills hypoxic tumor cells in mice", The Journal of Clinical Investigation, 2008, 118, 3930-3942, 17 pgs.
Olivier Feron, "Pyruvate into lactate and back: From the Warburg effect to symbiotic energy fuel exchange in cancer cells", Radiotherapy and Oncology 92 (2009) 329-333, 5 pgs.
Kelly M Kennedy, "Tumor metabolism of lactate: the influence and therapeutic potential for MCT and CD147 regulation", Future Oncol. (2010) 6(1), 127-148, 22 pgs.
Valéry L. Payen et al., "Common Responses of Tumors and Wounds to Hypoxia", vol. 21, No. 2, Mar./Apr. 2015, 75-87, 13 pgs.
Gabriela Jiménez-Valerio et al., "Resistance to Antiangiogenic Therapies by Metabolic Symbiosis in Renal Cell Carcinoma PDX Models and Patients", Cell Reports, 2016, 15, 1134-1143, 11 pgs.
Laura Pisarsky et al., "Targeting Metabolic Symbiosis to Overcome Resistance to Anti-angiogenic Therapy", Cell Reports 15, 2016, 1161-1174, 15 pgs.
Elizabeth Allen et al., "Metabolic Symbiosis Enables Adaptive Resistance to Anti-angiogenic Therapy that Is Dependent on mTOR Signaling", Cell Reports 15, May 10, 2016, 1144-1160, 18 pgs.
Kai-Stefan Dimmer, "The low-affinity monocarboxylate transporter MCT4 is adapted to the export of lactate in highly glycolytic cells", Biochem. J. (2000) 350, 219-227, 9 pgs.
Jocelyn E. Manning Fox et al., "Characterisation of human monocarboxylate transporter 4 substantiates its role in lactic acid efflux from skeletal muscle", Journal of Physiology (2000), 529.2, pp. 285-293, 9 pgs.
Johanna Chiche et al., "In vivo pH in metabolic-defective Ras-transformed fibroblast tumors: key role of the monocarboxylate transporter, MCT4, for inducing an alkaline intracellular pH", Int. J. Cancer: 130, 2012, 1511-1520, 10 pgs.
Mohammed S. Ullah et al., "The Plasma Membrane Lactate Transporter MCT4, but Not MCT1, Is Up-regulated by Hypoxia through a HIF-1α-dependent Mechanism", The Journal of Chemistry, vol. 281, No. 14, Apr. 7, 2006, pp. 9030-9037, 13 pgs.
Andrew P. Halestrap, "The Monocarboxylate Transporter Family—Structure and Functional Characterization", IUBMB Life, 64(1): 1-9, Jan. 2012, 9 pgs.
F. Baltazar, "Monocarboxylate transporters as targets and mediators in cancer therapy response", Histol Histopathol (2014) 29: 1511-1524, 15 pgs.
Céline Pinheiro et al., "Role of monocarboxylate transporters in human cancers: state of the art", J Bioenerg Biomembr (2012) 44:127-139, 13 pgs.
Vera Miranda-Goncalves et al., "Monocarboxylate transporters (MCTs) in gliomas: expression and exploitation as therapeutic targets", Neuro-Oncology 15(2):172-188, 2013, 17 pgs.
Julieta Afonso, "CD147 and MCT1-Potential Partners in Bladder Cancer Aggressiveness and Cisplatin Resistance", Molecular Carcinogenesis 54:1451-1466 (2015), 16 pgs.
Nihed Draoui et al., "Synthesis and pharmacological evaluation of carboxycoumarins as a new antitumor treatment targeting lactate transport in cancer cells", Bioorganic & Medicinal Chemistry 21 (2013) 7107-7117, 11 pgs.
Nihed Draoui et al., "Antitumor Activity of 7-Aminocarboxycoumarin Derivatives, a New Class of Potent Inhibitors of Lactate Influx but Not Efflux", Mol Cancer Ther; 13(6) Jun. 2014, 10 pgs.
Valquiria Bueno et al., "The Specific Monocarboxylate Transporter (MCT1) Inhibitor, AR-C117977, a Novel Immunosuppressant, Prolongs Allograft Survival in the Mouse", Transplantation 2007, 84, 1204-1207, 4 pgs.
Matthew J. Ovens, "AR-C155858 is a potent inhibitor of monocarboxylate transporters MCT1 and MCT2 that binds to an intracellular site involving transmembrane helices 7-10", Biochem. J. (2010) 425, 523-530, 9 pgs.
Susan E. Critchlow et al., "Abstract 3224: Pre-clinical targeting of the metabolic phenotype of lymphoma by AZD3965, a selective inhibitor of monocarboxylate transporter 1 (MCT1)", Cancer Research, Published Apr. 15, 2012, 3 pgs.
Clare N. Gallagher et al., "The human brain utilizes lactate via the tricarboxylic acid cycle: a 13C-labelled microdialysis and high-resolution nuclear magnetic resonance study", 2009: 132; 2839-2849, 11 pgs.
L. P. B. Goncalves et al., "Enzymatic Laboratory Scale Production of Homochiral (R)-3-Fluorolactic Acid Methyl Ester via Enantiospecific Reduction of Sodium Fluoropyruvate Catalyzed by Rabbit Muscle L-Lactate Dehydrogenase (L-LDH).", Tetrahedron: Asymmetry, vol. 7, No. 5, pp. 1237-1240, 1996, 4 pgs.
Ralf Schirrmacher et al., "Alpha selective epoxide opening with 18F$^-$: synthesis of 4-(3-[18F]fluoro-2-hydroxypropoxy)benzaldehyde ([18F]FPB) for peptide labeling", Tetrahedron Letters 52 (2011) 1973-1976, 4 pgs.
Shin Ae Park et al., "Epoxide Opening with Tetrabutylammonium Fluoride (TBAF)", Bull. Korean Chem. Soc. 2007, vol. 28, No. 10, 3 pgs.
CJ De Saedeleer et al., "Glucose deprivation increases monocarboxylate transporter 1 (MCT1) expression and MCT1-dependent tumor cell migration", Oncogene (2014) 33, 4060-4068, 9 pgs.
Vincent F. Van Hée et al., "Lactate does not activate NF-kB in oxidativet umor cells", Front. Pharmacol., Oct. 2015, vol. 6, Article228, 12 pgs.
Cyril Corbet et al., "The SIRT1/HIF2a Axis Drives Reductive Glutamine Metabolism under Chronic Acidosis and Alters Tumor Response to Therapy", Cancer Res; 74(19) 5507-19, 2014, 13 pgs.
Nisha Vijay et al., "A Novel Monocarboxylate Transporter Inhibitor as a Potential Treatment Strategy for γ-Hydroxybutyric Acid Overdose", Pharm Res (2015) 32:1894-1906, 13 pgs.
Translation of International Search Report dated Dec. 1, 2017 and Written Opinion in corresponding International application No. PCT/EP2017/072582; 7 pages.

[$^{18}$F]-LABELLED LACTATE DERIVATIVE AS PET RADIOTRACER

FIELD

The present invention relates to a positron emission tomography (PET) radiotracer for imaging lactate uptake, wherein the tracer is [$^{18}$F]-3-fluoro-2-hydroxypropionic acid or a salt thereof, preferably a salt of [$^{18}$F]-3-fluoro-2-hydroxypropionate, also named [$^{18}$F]-3-fluorolactate or [$^{18}$F]-3-fluoro-2-hydroxypropanoate. The invention also provides a process for the radiosynthesis of [$^{18}$F]-3-fluoro-2-hydroxypropionic acid. The invention further relates to the use of [$^{18}$F]-3-fluoro-2-hydroxypropionic acid for imaging lactate uptake in living cells, especially in humans.

BACKGROUND

Lactic acid plays a role in several biochemical processes. At physiological pH, lactic acid (pKa 3.86) is fully dissociated in lactate and proton.

In vivo, L-(+)-lactate is produced from pyruvate by lactate dehydrogenase (LDH) enzymes, in a process of fermentation during metabolism. Lactate is produced in cells and its level is regulated by various factors including oxygen availability and monocarboxylate transporters (MCT). MCTs are passive transporters, among which MCT1 to MCT4 can transport lactate.

Lactate is implicated to provide energy during exercise. It also plays an important role in brain metabolism. Various disorders imply lactate uptake and/or are characterized by deregulated lactate levels, such as for example cancer, fatigue syndromes, cryptic exercise intolerance, exercise-induced hyperinsulinemia, severe X-linked psychomotor retardation, immune diseases, age-related cognitive impairment, amnesia, Alzheimer's disease, epilepsy, diabetes, hypoglycemia and obesity (Halestrap, Mol Aspects Med, 2013, 34, 337-349; Tsai et al., Front Aging Neurosci 2016, 8, 57; Pérez-Escuredo et al., BBA Mol Cell Res, 2016, 1863, 2481-2497; Brinkmann et al., J Diabetes Complications, 2015, 27, 965-969; Carneiro et al., Obes Rev 2015, 16 Suppl 1, 55-66).

Metabolic plasticity is a hallmark of cancer cells allowing them to optimally use existing resources for energy production and biosynthesis. Among possible fuels, lactate singles out as it is at the core of a metabolic cooperation between glycolytic cancer cells that produce lactate and oxidative cancer cells that use lactate (Sonveaux et al., J Clin Invest, 2008, 118, 3930-3942). This cooperation is of symbiotic nature: by delivering lactate to oxidative cancer cells that have a metabolic preference for lactate compared to glucose, glycolytic cancer cells facilitate glucose diffusion and use in the hypoxic/glycolytic cancer compartment (Feron et al., Radiother Oncol, 2009, 92, 329-333; Kennedy et al., Future Oncol, 2010, 6, 127-148; Pérez-Escuredo et al., BBA Mol Cell Res, 2016, 1863, 2481-2497). Together with other processes, metabolic cooperativity represents an evolutionary solution for cancer cell survival and proliferation in a metabolically altered environment (Payen et al., Cancer J, 2015, 21, 75-87).

Metabolic cooperation can be mobilized as a mode of resistance to anti-angiogenic therapies (Jimenez-Valerio G et al., Cell Rep, 2016, 15: 1134-43; Pisarsky L et al., Cell Rep, 2016, 15: 1161-74; Allen E et al., Cell Rep, 2016, 15: 1144-60. Overall, it depends on the expression and activity of members of the MCTs family that are located at the cell membrane (Halestrap, Mol Aspects Med, 2013, 34, 337-349; Pisarsky et al., Cell Reports, 2016, 15, 1161-1174): MCT4 is the main facilitator of lactate export by glycolytic cancer cells (Dimmer et al., Biochem J, 2000, 350 Pt 1: 219-27; Manning Fox et al., J Physiol, 2000, 529 Pt 2: 285-93; Chiche et al., Int J Cancer, 2012, 130(7), 1511-1520), and MCT1 primarily conveys lactate uptake by oxidative cancer cells (Ullah et al., J Biol Chem, 2006, 281, 9030-9074; Halestrap, IUBMB Life, 2012, 64, 1-9). Compared to MCT1 and MCT4, MCT2 and MCT3 are less often expressed in cancers (Pérez-Escuredo et al., BBA Mol Cell Res, 2016, 1863, 2481-2497).

Such metabolic cooperation is found in a variety of human cancers of different histological types, including head and neck, breast, lung, stomach, colon, bladder, prostate and cervix cancers, as well as gliomas (Baltazar et al., Histol Histopathol, 2014, 29, 1511-1524; Pinheiro et al., J Bioenerg Biomembr, 2012, 44, 127-139; Miranda-Goncalves et al., Neuro Oncol, 2013, 15, 172-188; Afonso et al., Mol Carcinog, 2015, 54, 1451-1466).

This motivated the development and preclinical evaluation of several MCT inhibitors (Draoui et al., Bioorg Med Chem, 2013, 21, 7107-7117; Draoui et al., Mol Cancer Ther, 2014, 13, 1410-1418; Bueno et al., Transplantation, 2007, 84, 1204-1207; Ovens et al., Biochem J, 2010, 425, 523-530; Critchlow et al., Cancer Res, 2012, 72, 3224), of which AZD3965 is currently evaluated as an anticancer agent in Phase I clinical trials for patients with prostate cancer, gastric cancer or diffuse large B cell lymphoma (ClinicalTrials.gov NCT01791595). The related compound AR-C155858 is a selective MCT1 inhibitor that nevertheless also inhibits MCT2, but only when it is bound to ancillary protein basigin, whereas its preferred chaperone protein is embigin (Ovens et al., Biochem J, 2010, 425, 523-530).

Although MCT1 inhibitors are being actively developed and AZD3965 recently entered into clinical trials for the treatment of cancer, the measurement of lactate uptake and its inhibition in clinical settings is still an unmet clinical need.

Consequently, it is important to be able to image lactate flux in vivo either to image the response of tumors but also pathologies other than cancer, as well as to understand the role of lactate and to determine tissues that take up lactate.

A $^{13}$C-labelled lactate was described for that purpose (Gallagher et al., Brain, 2009, 132:2839-2849). It may be imaged by dynamic polarization (DNP), for preclinical use. However, the very short half-life of $^{13}$C and required sophisticated equipment for $^{13}$C imaging render applications for in vivo imaging quite limited.

A tracer able to image lactate uptake and overcoming the above drawbacks is thus needed.

Positron emission tomography (PET) is used in clinics with various tracers. $^{18}$F-fluorodeoxyglucose ($^{18}$F-FDG), also known as 2-deoxy-2-($^{18}$F)fluoro-D-glucose, is for example used to measure glucose uptake and allows to detect cancers and their metastases in patients. $^{18}$F-FDG is in routine clinical use.

Therefore, providing a PET lactate tracer, labelled with $^{18}$F, is of major interest since $^{18}$F labelling and detection are commonly performed in clinics, and clinical settings already present in hospital may be easily adapted. The radioactive half-life of $^{18}$F is 110 min.

A suitable $^{18}$F-labelled lactate tracer should meet the following specifications:
 the $^{18}$F-tracer should be chemically stable, before administration, but also after administration;
 the labelling of lactate with $^{18}$F should not affect the uptake;

the labelling of lactate with $^{18}F$ should maintain lactate functionality, i.e. its transport by lactate transporters and its transformation in pyruvate and downstream metabolites of pyruvate into cells, in order to enable its accumulation inside cells;

the $^{18}F$-tracer should be selective for lactate transporters;

the $^{18}F$-tracer should not inhibit lactate transporters;

the $^{18}F$-tracer should release as few as possible $^{18}F$.

Based on the chemical structures of known substrates of MCTs, i.e. lactate and bromo-pyruvate (see scheme 1), (±)-[$^{18}F$]-3-fluoro-2-hydroxypropionic acid was investigated as a potential $^{18}F$-labelled lactate tracer. This approach involves the bioisosteric replacement of an H-atom in the 3-position of lactate with a fluorine.

Scheme 1. Structures of (+)-lactic acid, 3-bromopyruvic acid and (±)-[$^{18}F$]-3-fluoro-2-hydroxypropionic acid.

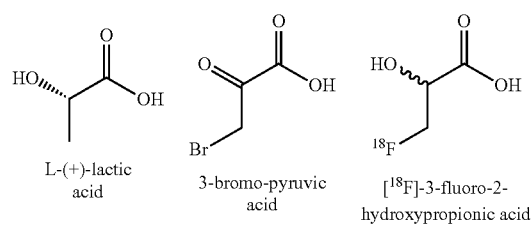

L-(+)-lactic acid   3-bromo-pyruvic acid   [$^{18}F$]-3-fluoro-2-hydroxypropionic acid Although the replacement of a hydrogen atom with a fluorine is usually reported to afford bioisosteric compounds, its introduction, in the present case, in the 3-position of lactate was very challenging because:

(i) to the Applicant's knowledge, even if 3-fluoro-2-hydroxypropionate was already disclosed (WO2010/088564, FR2290417, Goncalves et al., Tetrahedron Assym., 1996, 7(5), 1237-1240), the $^{18}F$-labelled compound was never reported before, and in the prior art disclosing nonradioactive 3-fluoro-2-hydroxypropionate, no chemical synthesis is disclosed; and (ii) because of its high electronegativity, the fluorine atom could impact the electronic surrounding of the molecule, thus affecting its proper recognition by MCTs, especially MCT1, and metabolism by lactate dehydrogenases (LDHs).

For $^{18}F$ introduction, an epoxide opening with fluorine was envisioned. However, the preparation of the $^{18}F$-labelled compound through this route was highly challenging because the epoxide opening with fluorine, that is known to be favored at the least substituted carbon in the presence of an electron-donating group at the epoxide α-position (Schirrmacher et al., Tetrahedron Letters, 52(16), 1973-1976; Park et al., Bull Korean Chem Soc, 2007, 28(10), 1834-1836), has never been investigated previously in the presence of an electron-attracting group at this α-position, and, in the present case, a carboxylate is found in that position.

Strikingly, it is herein demonstrated for the first time the synthesis of (±)-[$^{18}F$]-3-fluoro-2-hydroxypropionate in a good radiochemical yield and with an excellent regioselectivity, i.e. in favor of the targeted (±)-[$^{18}F$]-3-fluoro-2-hydroxypropionate vs. the (±)-[$^{18}F$]-2-fluoro-3-hydroxypropionate regioisomer.

Regarding the potential impact of the fluorine atom on the tracer metabolism by lactate dehydrogenases (LDHs) and thus on its accumulation in cells, performing a preliminary assay of conversion by LDH was needed. However, at the time of this study, nonradioactive 3-fluoro-2-hydroxypropionate was not commercially available and could not be successfully synthesized by the Applicant. Therefore, the Applicant verified instead that available 3-fluoropyruvate could be converted to 3-fluoro-2-hydroxypropionate by LDH, which is a bidirectional enzyme. Obtained data (see experimental part II.1) supported the possibility that (±)-[$^{18}F$]-3-fluoro-2-hydroxypropionate could be metabolized to [$^{18}F$]-3-fluoropyruvate by LDH, i.e., along the oxidative pathway of lactate in oxidative cancer cells.

The Applicant also herein provides the preclinical validation of (±)-[$^{18}F$]-3-fluoro-2-hydroxypropionate as a tracer of lactate uptake for positron emission tomography (PET). (±)-[$^{18}F$]-3-fluoro-2-hydroxypropionate was generated in clinical settings and evaluated in the same cancer model that served for the discovery of the metabolic symbiosis of cancers. It was further validated preclinically in another different model of cancer.

As evidenced in the experimental part (parts II.2, II.3 and II.4), (±)-[$^{18}F$]-3-fluoro-2-hydroxypropionate fulfills the required specifications of a PET tracer. Especially, (±)-[$^{18}F$]-3-fluoro-2-hydroxypropionate is actively taken up and retained by oxidative cancer cells that consume lactate in vitro, and accumulates in tumors and tissues known to consume lactate in vivo, which is efficiently prevented by a pharmacological inhibition of the inward lactate transporter MCT1. Used pharmacological inhibitors of MCT1 were AR-C155858 and AZD3965, already mentioned above.

[$^{18}F$]-3-fluoro-2-hydroxypropionate can be used as a PET tracer of lactate uptake. In oncology, [$^{18}F$]-3-fluoro-2-hydroxypropionate could be used as a tool to predict and document a response to pharmacological agents and treatments aimed at disrupting lactate use and consumption by tumors, thus allowing to adapt treatment on an individual scale. For predicting a response to pharmacological agents and treatments aimed at disrupting lactate use and consumption by tumors, [$^{18}F$]-3-fluoro-2-hydroxypropionate can be administered to tumor patients, and if it accumulates in the tumor thus providing a positive signal in PET scan, the tracer would indicate that the tumor takes up lactate and that the patient would benefit from receiving pharmacological agents and treatments aimed at disrupting lactate use and consumption by tumors. For documenting a biological response to pharmacological agents and treatments aimed at disrupting lactate use and consumption by tumors, [$^{18}F$]-3-fluoro-2-hydroxypropionate can be administered before and after such treatment, and a decrease in tracer uptake would been seen by a reduced PET signal would indicate that the tumor of the patient is responding to pharmacological agents and treatments aimed at disrupting lactate use and consumption by tumors.

In other pathologies, [$^{18}F$]-3-fluoro-2-hydroxypropionate could be used as a diagnostic tool to evidence altered lactate metabolism. These pathologies include for example fatigue syndromes, cryptic exercise intolerance, exercise-induced hyperinsulinemia, severe X-linked psychomotor retardation, immune diseases, age-related cognitive impairment, amnesia, Alzheimer's disease, epilepsy, diabetes, hypoglycemia and obesity (Halestrap, Mol Aspects Med, 2013, 34, 337-349; Tsai et al., Front Aging Neurosci 2016, 8, 57; Pérez-Escuredo et al., BBA Mol Cell Res, 2016, 1863, 2481-2497; Brinkmann et al. J Diabetes Complications, 2015, 27, 965-969; Carneiro et al., Obes Rev 2015, 16 Suppl 1, 55-66).

SUMMARY

This invention thus relates to a compound which is [$^{18}F$]-3-fluoro-2-hydroxypropionic acid:

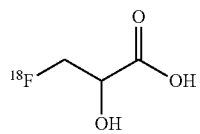

or a pharmaceutically acceptable salt and/or solvate thereof.

According to one embodiment, the salt is [$^{18}$F]-3-fluoro-2-hydroxypropionate sodium salt.

The invention also relates to a pharmaceutical composition comprising the compound of the invention, and at least one pharmaceutically acceptable excipient. The invention also relates to a medicament comprising the compound of the invention.

The invention further relates to the use of the compound of the invention, for positron emission tomography imaging. It also relates to the use of the compound of the invention for positron emission tomography imaging of lactate uptake by cells.

The invention also relates to a compound of the invention for use in determining cells or populations of cells of an individual taking up lactate and/or having alterations in lactate uptake.

The invention also relates to a compound of the invention for use in predicting and/or monitoring if a tumor of an individual displays a therapeutic response to treatments modulating lactate uptake and/or lactate metabolism. According to an embodiment, the treatment modulating lactate uptake is selected from drugs inhibiting MCTs, preferably drugs inhibiting MCT1. According to an embodiment, the treatment modulating lactate metabolism is selected from drugs inhibiting LDH, preferably drugs inhibiting LDHB, MPC or ALT.

The invention also relates to a method for in vitro detection of lactate uptake in a tissue, said method comprising
(1) contacting said tissue with an amount of the compound of the invention, sufficient to be detected by PET;
(2) forming at least one PET image; and
(3) determining lactate uptake by observing the image.

The invention also relates to a compound of the invention for use in imaging diseases, said method comprising
(1) administering to an individual an amount of the compound of the invention sufficient to be detected by PET; and
(2) forming at least one PET image showing the distribution of the compound of the invention, within the individual.

The invention also relates to a compound of the invention for use in monitoring a disease therapy in an individual, said method comprising
(1) administering to said individual an amount of the compound of the invention, sufficient to achieve imaging; and
(2) performing imaging using PET by detecting a signal from the compound of the invention, within the individual, to follow the response of the individual to the therapy.

The invention further relates to a process of manufacturing of [$^{18}$F]-3-fluoro-2-hydroxypropionic acid or a pharmaceutically acceptable salt and/or solvate thereof, comprising the following steps:
a) an epoxide-ring opening reaction on benzyl oxirane-2-carboxylate (II)

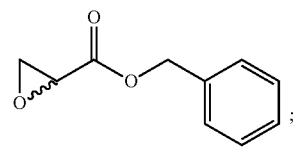

in presence of [$^{18}$F]-fluoride, to afford [$^{18}$F]-benzyl 3-fluoro-2-hydroxypropionate (III*)

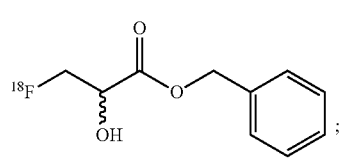

and
b) hydrolysis of [$^{18}$F]-benzyl 3-fluoro-2-hydroxypropionate (III*) to afford [$^{18}$F]-3-fluoro-2-hydroxypropionic acid or a pharmaceutically acceptable salt and/or solvate thereof.

According to one embodiment, the process accordingly comprises a preliminary step of synthesis of benzyl oxirane-2-carboxylate (II) by epoxidation of benzyl acrylate (I).

Definitions

In the present invention, the following terms have the following meanings:

"About", preceding a figure, means plus or less 10% of the value of said figure.

An "individual" refers to an animal, preferably a mammal, more preferably a human, receiving the compound of the invention.

By "imaging of lactate uptake" it is referred to relative or absolute quantification of the uptake of lactate by cells.

By "alterations in lactate uptake" it is referred to any change in the uptake of lactate by cells.

By "therapeutic response to treatments modulating lactate uptake" it is referred to any change in the uptake of lactate by cells induced by a treatment.

By "therapeutic response to treatments modulating lactate metabolism" it is referred to any change in the metabolism of lactate induced by a treatment.

"Pharmaceutically acceptable excipient" refers to an excipient that does not produce an adverse, allergic or other untoward reaction when administered to an animal, preferably a human. It includes any and all solvents, dispersion media, coatings, antibacterial and antifungal agents, isotonic and absorption delaying agents and the like. For human administration, preparations should meet sterility, pyrogenicity, general safety and purity standards as required by regulatory offices, such as, for example, FDA Office or EMA.

"Solvate" is used herein to describe a molecular complex comprising the compound of the invention and one or more pharmaceutically acceptable solvent molecules, for example, ethanol or water. When the solvent is water, the solvate is also named "hydrate".

DETAILED DESCRIPTION

[$^{18}$F]-3-fluoro-2-hydroxypropionate

This invention relates to a compound which is [$^{18}$F]-3-fluoro-2-hydroxypropionic acid:

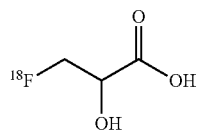

or a pharmaceutically acceptable salt and/or solvate thereof.

[$^{18}$F]-3-fluoro-2-hydroxypropionate is also named [$^{18}$F]-3-fluorolactate or [$^{18}$F]-3-fluoro-2-hydroxypropanoate.

[$^{18}$F]-3-fluoro-2-hydroxypropionate is chiral and exists under two optical isomeric forms. According to one embodiment, the invention relates to (+)-[$^{18}$F]-3-fluoro-2-hydroxypropionate. In another embodiment, the invention relates to (−)-[$^{18}$F]-3-fluoro-2-hydroxypropionate. In a further embodiment, the invention relates to the racemate, (±)-[$^{18}$F]-3-fluoro-2-hydroxypropionate. In the present invention, the use of the term "[$^{18}$F]-3-fluoro-2-hydroxypropionate" encompasses reference to each of the enantiomers as well as mixtures thereof in any ratio.

The compound of the invention may be in the form of a salt, preferably a pharmaceutically acceptable salt. Pharmaceutically acceptable salts include the base salts thereof. Suitable base salts are formed from bases which form non-toxic salts. Examples include the ammonium, aluminum, arginine, benzathine, calcium, chloroprocaine, choline, diethylamine, diethanolamine, 2-(diethylamino)ethanol, diolamine, ethanolamine, ethylenediamine, glycine, lithium, lysine, magnesium, meglumine, N-methyl-glutamine, morpholine, olamine, ornithine, piperazine, potassium, procaine, sodium, tris(hydroxymethyl)aminomethane, tromethamine, 4-(2-hydroxyethyl)morpholine, N-benzylphenethyl-amine, and zinc salts. Hemisalts of bases may also be formed, for example, hemisulphate and hemicalcium salts.

Pharmaceutically acceptable salts may be prepared (i) by reacting the compound of the invention with the desired base; and/or (ii) by converting one salt of the compound of the invention to another by reaction with an appropriate base or by means of a suitable ion exchange column. These reactions are typically carried out in solution. The salt, may precipitate from solution and be collected by filtration or may be recovered by evaporation of the solvent. The degree of ionization in the salt may vary from completely ionized to almost non-ionized.

The compound of the invention may be in the form of a solvate, preferably a pharmaceutically acceptable solvate. Pharmaceutically acceptable solvates refer to molecular complexes comprising the compound of the invention and one or more pharmaceutically acceptable solvent molecules, for example, ethanol or water.

Process of Manufacturing

The present invention also relates to a process for manufacturing [$^{18}$F]-3-fluoro-2-hydroxypropionate and pharmaceutically acceptable salts and/or solvates thereof. The route of synthesis of the invention is summarized in the scheme below:

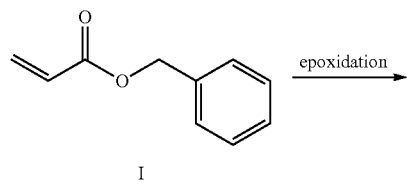

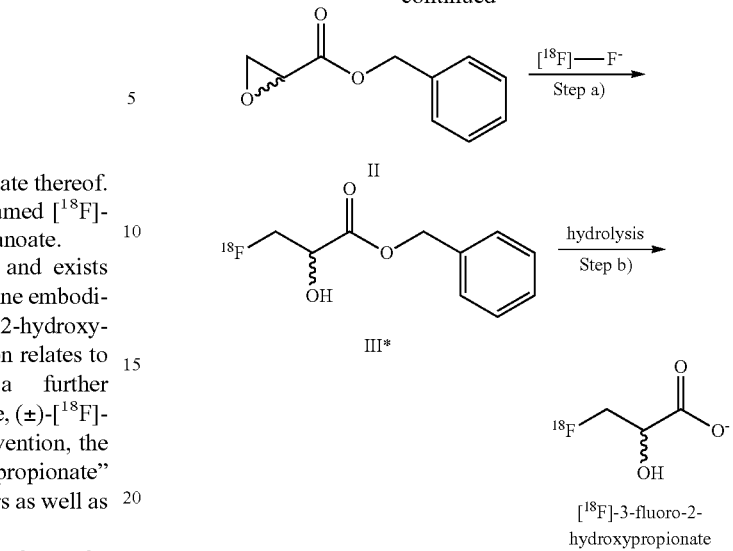

According to one embodiment, the process of the invention comprises the following steps:

a) an epoxide-ring opening reaction on benzyl oxirane-2-carboxylate (II)

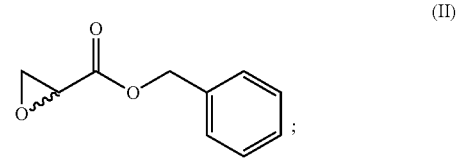 [SMILES: O=C(OCc1ccccc1)C1CO1]

in presence of [$^{18}$F]-fluoride, to afford [$^{18}$F]-benzyl 3-fluoro-2-hydroxypropionate (III*)

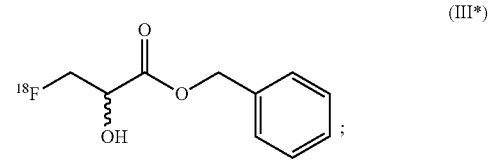 [SMILES: O=C(OCc1ccccc1)C(O)C[18F]]

and b) hydrolysis of [$^{18}$F]-benzyl 3-fluoro-2-hydroxypropionate (III*) to afford [$^{18}$F]-3-fluoro-2-hydroxypropionic acid or a pharmaceutically acceptable salt and/or solvate thereof.

In one embodiment, the process of the invention is performed on a remote-controlled synthesis apparatus.

Step a)

In one embodiment, [$^{18}$F]-fluoride is generated on a cyclotron, preferably a medical isotope cyclotron, from the nuclear reaction $^{18}$O(p,n)$^{18}$F. According to one embodiment, [$^{18}$F]-fluoride is isolated from water of irradiation on an anionic cartridge, such as for example a Chromafix 30-PS-HCO$_3$ cartridge. [$^{18}$F]-fluoride is then retrieved from the cartridge by ion exchange and elution in a basic solution. In one embodiment, the basic solution is selected from solution of K$_2$CO$_3$, tetrabutylammonium hydroxide (TBAOH), tetrabutylammonium carbonate (TBAHCO$_3$), potassium methasulfonate, a mixture K$_2$C$_2$O$_4$/2.2.2 cryptand (wherein 2.2.2 cryptand is preferably Kryptofix 2.2.2, which corresponds to 4,7,13,16,21,24-hexaoxa-1,10-diazabicyclo-(8.8.8)-hexacosane) or a mixture thereof. Alternative counter ions to potassium may also be used. In one embodiment, the solvent of the basic solution is acetonitrile, water, methanol or a mixture thereof. In a specific embodiment, [$^{18}$F]-fluoride is retrieved from the cartridge by elution with an aqueous solution of $K_2C_2O_4$/kryptofix 2.2.2 (with a molar ratio of 1/2) diluted in methanol.

According to one embodiment, [$^{18}$F]-fluoride used in step a) is selected from [$^{18}$F]-KF, and [$^{18}$F]-TBAF (tetrabutylammonium fluoride).

According one embodiment, [$^{18}$F]-fluoride used in step a) is anhydrous. Anhydrous [$^{18}$F]-fluoride may be obtained by azeotropic distillation of the solution eluted from the cartridge, preferably by azeotropic distillation with acetonitrile at 95° C. Preferably, azeotropic distillation is performed under inert atmosphere, such as for example under a stream of helium.

According to one embodiment, the process of the invention is performed at a pH ranging from 6 to 7.4, more preferably at a pH ranging from 6.9 to 7.1. These ranges of pH correspond to amounts of base used for retrieving [$^{18}$F]-fluoride from the cartridge into the reaction vessel which are lower compared to what is usually employed for [$^{18}$F]-fluoride retrieval, namely about ten time less base is used in the process of the invention. It was advantageously observed that performing the reaction in such conditions enables to improve the yield of the process, especially by favoring the opening of the epoxide ring and by improving the stability of intermediate (III*) and of final product [$^{18}$F]-3-fluoro-2-hydroxypropionate.

According to one embodiment, step a) is performed in a solvent selected from dimethylsulfoxide (DMSO) and 2-methyl-2-butanol. Preferably the solvent is anhydrous. According to a particularly preferred embodiment, step a) is performed in anhydrous 2-methyl-2-butanol as solvent. The use of 2-methyl-2-butanol, which is a protic solvent, has the effect to improve the regioselectivity of the formation of [$^{18}$F]-benzyl 3-fluoro-2-hydroxypropionate (III*) over [$^{18}$F]-benzyl 2-fluoro-3-hydroxypropionate (IV*).

According to one embodiment, step a) is performed at a temperature ranging from 90° C. to 150° C., preferably ranging from 100° C. to 125° C., more preferably ranging from 100° C. to 110° C.

According to one embodiment, step a) is performed for a duration ranging from 5 min to 30 min, preferably ranging from 5 min to 15 min, more preferably for about 10 min.

According to a specific embodiment, step a) is performed in anhydrous 2-methyl-2-butanol as solvent, at a temperature of 105° C. for 10 minutes.

According to an embodiment, the reaction mixture is passed through an alumina cartridge to eliminate unreacted [$^{18}$F]-fluoride.

In one embodiment, [$^{18}$F]-benzyl 3-fluoro-2-hydroxypropionate (III*) is isolated by high performance liquid chromatography (HPLC).

Step b)

According to one embodiment, the hydrolysis of step b) is performed in basic conditions. In one embodiment, hydrolysis is performed using a solid-phase extraction method, preferably using a C18 Sep-Pak cartridge and a solution of NaOH.

According to one embodiment, step b) is performed for a duration ranging from 1 min to 20 min, preferably ranging from 2 min to 10 min, more preferably for about 5 min.

According to an alternative embodiment, the hydrolysis of step b) is performed by enzymatic hydrolysis.

Preliminary Step

According to one embodiment, benzyl oxirane-2-carboxylate (II) is obtained by epoxidation of benzyl acrylate (I). According to one embodiment, epoxidation is performed in presence of a peroxyacid, such as for example 3-chloroperoxybenzoic acid (m-CPBA).

Pharmaceutical and Imaging Compositions

The present invention further relates to a pharmaceutical composition comprising [$^{18}$F]-3-fluoro-2-hydroxypropionic acid or a pharmaceutically acceptable salt and/or solvate thereof, and at least one pharmaceutically acceptable excipient.

The present invention also relates to an imaging composition comprising [$^{18}$F]-3-fluoro-2-hydroxypropionic acid or a pharmaceutically acceptable salt and/or solvate thereof, and at least one pharmaceutically acceptable excipient.

The compositions of the invention may comprise antioxidants, buffers, bacteriostatic agents and solutes which render the formulation isotonic.

The compound of the present invention may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable excipients, adjuvants and vehicles appropriate for each route of administration. Preferably the compound of the present invention is administered by oral or parenteral routes of administration.

The compositions for the administration of the compound of this invention may conveniently be presented in dosage unit form and may be prepared by any of the methods well known in the art of pharmacy, taking into account the short radioactive half-life of 18-fluor which is of 110 minutes. All methods include the step of bringing the active ingredient into association with the excipient which constitutes one or more accessory ingredients. In general, the pharmaceutical and imaging compositions are prepared by uniformly and intimately bringing the active ingredient into association with a liquid excipient or a finely divided solid excipient or both, and then, if necessary, shaping the product into the desired formulation. In the pharmaceutical and imaging compositions the active compound is included in an amount sufficient to produce the desired effect.

The compositions containing the active ingredient may be in a form suitable for oral use, for example aqueous or oily suspensions, dispersible powders or emulsions. Compositions intended for oral use may be prepared according to any method known to the art for the manufacture of pharmaceutical or imaging compositions and such compositions may contain one or more agents selected from the group consisting of sweetening agents, flavoring agents, coloring agents and preserving agents in order to provide pharmaceutically elegant and palatable preparations. Aqueous suspensions contain the active materials in admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzate, one or more coloring agents, one or more flavoring agents, and one or more sweetening agents, such as sucrose or saccharin. Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

The pharmaceutical and imaging compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution.

The composition may additionally comprise a stabilizer. Chemical stabilizers are useful to reduce the likelihood for radiolysis-induced decomposition of the 18F-labelled compound at high radioactivity concentrations. Suitable stabilizers include antioxidants such as sugar alcohol or sugar lactone, wherein the sugar alcohol is for example erythritol xylitol, sorbitol or mannitol and wherein the sugar lactone is for example ascorbic acid or glucono-o-lactone.

Imaging lactate uptake will generally involve a dose ranging from 1 MBq/kg body weight to 530 MBq of the compositions of the invention. It will be understood, however, that the specific dose level for any particular patient may be varied and will depend upon a variety of factors including the age, body weight, general health, sex, diet, mode and time of administration, rate of excretion, drug combination, the severity of the particular condition, and the host undergoing therapy.

The invention also relates to a kit comprising a sealed vial containing a predetermined quantity of [$^{18}$F]-3-fluoro-2-hydroxypropionic acid, or a pharmaceutically acceptable salt and/or solvate thereof.

Pharmaceutical Use

The present invention also relates to a medicament comprising [$^{18}$F]-3-fluoro-2-hydroxypropionic acid, or a pharmaceutically acceptable salt and/or solvate thereof. In one embodiment, the invention relates to [$^{18}$F]-3-fluoro-2-hydroxypropionic acid, or a pharmaceutically acceptable salt and/or solvate thereof for use as a medicament. In one embodiment, the invention relates to the use of [$^{18}$F]-3-fluoro-2-hydroxypropionic acid, or a pharmaceutically acceptable salt and/or solvate thereof, for the manufacture of a medicament.

The present invention also relates to [$^{18}$F]-3-fluoro-2-hydroxypropionic acid, or a pharmaceutically acceptable salt and/or solvate thereof for use as an imaging agent. In one embodiment, the invention relates to the use of [$^{18}$F]-3-fluoro-2-hydroxypropionic acid, or a pharmaceutically acceptable salt and/or solvate thereof, for the manufacture of an imaging agent.

In one embodiment, the imaging agent is an imaging agent for positron emission tomography (PET).

The invention also relates to the use of [$^{18}$F]-3-fluoro-2-hydroxypropionic acid, or a pharmaceutically acceptable salt and/or solvate thereof, for PET imaging.

The invention also relates to the use of [$^{18}$F]-3-fluoro-2-hydroxypropionic acid, or a pharmaceutically acceptable salt and/or solvate thereof, for PET imaging of lactate uptake by cells, preferably for PET imaging of lactate uptake in living cells or tissues, more preferably in living cells or tissues in mammals.

The invention also relates to the use of [$^{18}$F]-3-fluoro-2-hydroxypropionic acid, or a pharmaceutically acceptable salt and/or solvate thereof, to determine which tissues or cells of an individual do take up lactate.

The invention also relates to the use of [$^{18}$F]-3-fluoro-2-hydroxypropionic acid, or a pharmaceutically acceptable salt and/or solvate thereof, to determine pathophysiological effects of lactate uptake and/or metabolism.

The invention also relates to the use of [$^{18}$F]-3-fluoro-2-hydroxypropionic acid, or a pharmaceutically acceptable salt and/or solvate thereof, to determine organs or tissues of an individual with alterations in lactate uptake and/or metabolism. Such determination may be used for clinical research or for diagnostic.

The invention also relates to the use of [$^{18}$F]-3-fluoro-2-hydroxypropionic acid, or a pharmaceutically acceptable salt and/or solvate thereof, to determine which tumors of a given individual do take up lactate.

The invention also relates to the use of [$^{18}$F]-3-fluoro-2-hydroxypropionic acid, or a pharmaceutically acceptable salt and/or solvate thereof, to predict if a tumor of a given individual may display a therapeutic response to treatments modulating lactate uptake and/or metabolism. This use enables the prediction of a therapeutic response. For predicting a response to pharmacological agents and treatments aimed at disrupting lactate use and consumption by tumors, [$^{18}$F]-3-fluoro-2-hydroxypropionate can be administered to tumor patients, and if it accumulates in the tumor thus providing a positive signal in PET scan, the tracer would indicate that the tumor takes up lactate and that the patient would benefit from receiving pharmacological agents and treatments aimed at disrupting lactate use and consumption by tumors.

The invention also relates to the use of [$^{18}$F]-3-fluoro-2-hydroxypropionic acid, or a pharmaceutically acceptable salt and/or solvate thereof, to determine if a tumor of a given individual displays a therapeutic response to treatments modulating lactate uptake and/or metabolism. This use enables imaging and quantifying a therapeutic response. For documenting a biological response to pharmacological agents and treatments aimed at disrupting lactate use and consumption by tumors, [$^{18}$F]-3-fluoro-2-hydroxypropionate can be administered before and after such treatment, and a decrease in tracer uptake after treatment would been seen by a reduced PET signal and would indicate that the tumor of the patient is responding to pharmacological agents and treatments aimed at disrupting lactate use and consumption by tumors.

The invention also relates to the use of [$^{18}$F]-3-fluoro-2-hydroxypropionic acid, or a pharmaceutically acceptable salt and/or solvate thereof, as a diagnostic tool of pathologies implying altered lactate metabolism such as for example fatigue syndromes, cryptic exercise intolerance, exercise-induced hyperinsulinemia, severe X-linked psychomotor retardation, immune diseases, age-related cognitive impairment, amnesia, Alzheimer's disease, epilepsy, diabetes, hypoglycemia or obesity.

The invention also relates to the use of [$^{18}$F]-3-fluoro-2-hydroxypropionic acid, or a pharmaceutically acceptable salt and/or solvate thereof, to determine in vitro and/or in vivo efficacy of treatments aimed at modulating lactate uptake and/or metabolism by cells and tissues. In one embodiment, the invention relates to the use of [$^{18}$F]-3-fluoro-2-hydroxypropionic acid, or a pharmaceutically acceptable salt and/or solvate thereof, to determine in vitro efficacy of treatments aimed at modulating lactate uptake and/or metabolism by cancer cells. In one embodiment, the invention relates to the use of [$^{18}$F]-3-fluoro-2-hydroxypropionic acid, or a pharmaceutically acceptable salt and/or solvate thereof, to determine in vivo efficacy of treatments aimed at modulating lactate uptake and/or metabolism by tumors.

In one embodiment, the treatment modulating lactate uptake is a treatment inhibiting lactate uptake. In one embodiment, the treatment inhibiting lactate uptake is a drug inhibiting MCTs, preferably a drug inhibiting MCT1. In one embodiment, the treatment inhibiting lactate uptake is a drug inhibiting other lactate transporters such as SMCTs. In one embodiment, the treatment inhibiting lactate uptake is a drug inhibiting the oxidative pathway of lactate. In another embodiment, the treatment inhibiting the oxidative pathway of lactate, is a LDH inhibitor. In yet another embodiment, the treatment inhibiting the oxidative pathway of lactate is an inhibitor of the mitochondrial pyruvate carrier (MPC). In yet another embodiment, the treatment inhibiting the oxidative pathway of lactate is an inhibitor of alanine transaminase (ALT).

The invention also relates to a method to detect lactate uptake in a cell or a population of cells, said method comprising
(1) administering an amount of [$^{18}$F]-3-fluoro-2-hydroxypropionic acid, or a pharmaceutically acceptable salt and/or solvate thereof, sufficient to be detected by PET;
(2) forming at least one PET image showing the distribution of [$^{18}$F]-3-fluoro-2-hydroxypropionic acid, or pharmaceutically acceptable salt and/or solvate thereof, within cell or population of cells; and
(3) determining lactate uptake by observing the image.

In one embodiment, the population of cells is a tissue or an organ, preferably a tissue or an organ from a mammal.

In one embodiment, [$^{18}$F]-3-fluoro-2-hydroxypropionic acid, or a pharmaceutically acceptable salt and/or solvate thereof, is used to image a broad variety of organs and/or tissues, including prostate, blood, lymph, ovary, cervix, bladder, breast liver, kidney, heart and brain.

In one embodiment, in the method to detect lactate uptake, the cell or population of cells is in a living mammal and the method is performed in vivo. In another embodiment, the method to detect lactate uptake is performed in vitro.

In one embodiment, when the method to detect lactate uptake is performed in vivo, the administration is performed by injecting a pharmaceutical composition as described above, into a blood vessel of the mammal. In another embodiment, the administration is performed orally, using a pharmaceutical composition as described above.

In one embodiment, the method enables to detect lactate uptake in cancer cells. In one embodiment, the method enables to detect a tumor. In one embodiment, the method enables to predict if a tumor may display a therapeutic response to a treatment modulating lactate uptake, especially an MCT inhibitor, preferably an MCT1 inhibitor. In one embodiment, the method enables to determine if a tumor displays a therapeutic response to a treatment modulating lactate uptake.

In one embodiment, in the method to detect lactate uptake, the effective amount of [$^{18}$F]-3-fluoro-2-hydroxypropionic acid, or pharmaceutically acceptable salt and/or solvate thereof, is ranging from 1 MBq/kg body weight to 530 MBq.

In one embodiment, the invention relates to a method for in vitro detection of lactate uptake in a tissue, said method comprising
(1) contacting said tissue with an amount of [$^{18}$F]-3-fluoro-2-hydroxypropionic acid, or a pharmaceutically acceptable salt and/or solvate thereof, sufficient to be detected by PET;
(2) forming at least one PET image; and
(3) determining lactate uptake by observing the image.

In one embodiment, the invention relates to a method to image diseases, said method comprising
(1) administering to an individual an amount of [$^{18}$F]-3-fluoro-2-hydroxypropionic acid, or a pharmaceutically acceptable salt and/or solvate thereof, sufficient to be detected by PET; and
(2) forming at least one PET image showing the distribution of [$^{18}$F]-3-fluoro-2-hydroxypropionic acid, or pharmaceutically acceptable salt and/or solvate thereof, within the individual.

In one embodiment, the invention relates to a method of diagnostic imaging or monitoring an individual, said method comprising
(1) administering to said individual an amount of [$^{18}$F]-3-fluoro-2-hydroxypropionic acid, or a pharmaceutically acceptable salt and/or solvate thereof, sufficient to achieve diagnostic imaging; and
(2) performing diagnostic imaging using PET by detecting a signal from [$^{18}$F]-3-fluoro-2-hydroxypropionic acid, or pharmaceutically acceptable salt and/or solvate thereof, within the individual.

In one embodiment, the invention relates to a method of monitoring a disease therapy in an individual, said method comprising
(1) administering to said individual an amount of [$^{18}$F]-3-fluoro-2-hydroxypropionic acid, or a pharmaceutically acceptable salt and/or solvate thereof, sufficient to achieve imaging; and
(2) performing imaging using PET by detecting a signal from [$^{18}$F]-3-fluoro-2-hydroxypropionic acid, or pharmaceutically acceptable salt and/or solvate thereof, within the individual, to follow the response of the individual to the therapy.

In one embodiment, the disease therapy is a cancer therapy, preferably a therapy using a MCT inhibitor, more preferably a MCT1 inhibitor.

EXAMPLES

Figure 1:
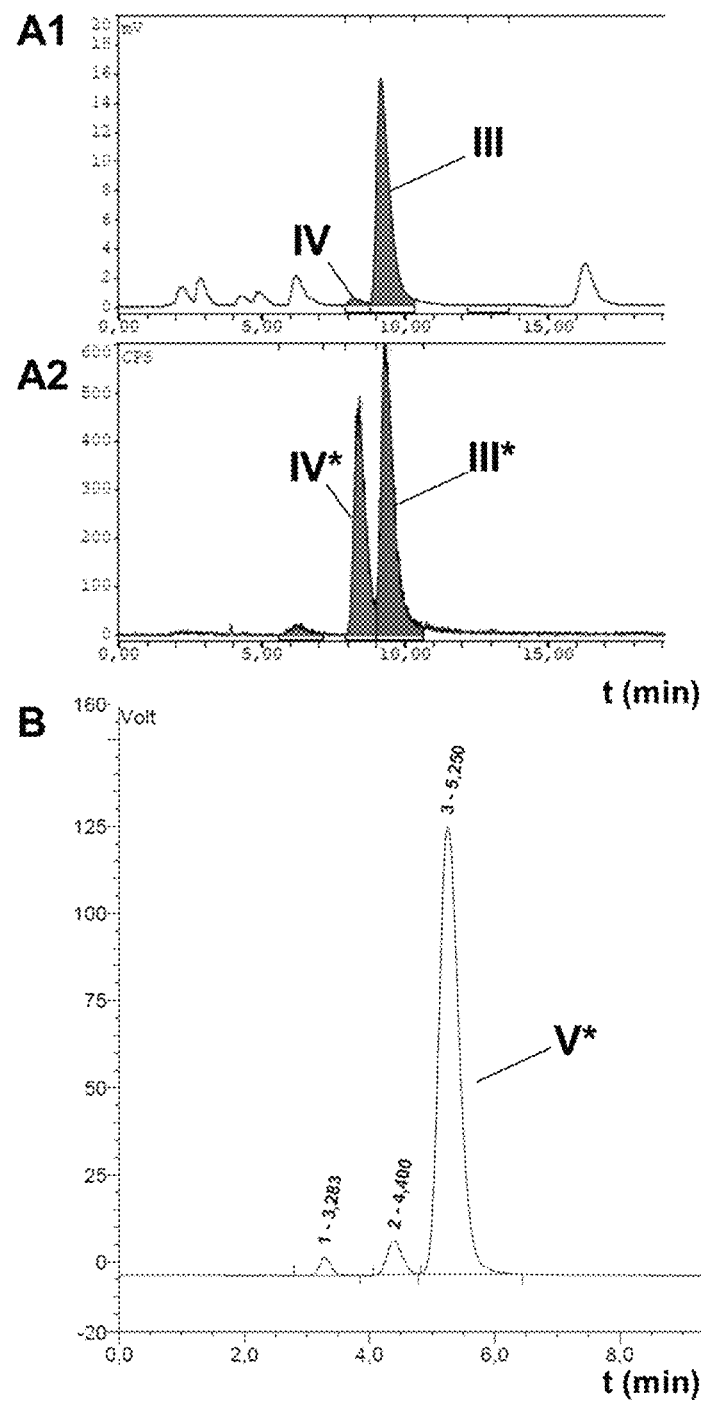
FIG. 1. A, Co-elution spectra of (±)-[$^{18}$F]-benzyl 3-fluoro-2-hydroxypropionate (III*) and nonradioactive benzyl 3-fluoro-2-hydroxypropionate (III), and (±)-[$^{18}$F]-2-fluoro-3-hydroxybenzylacrylate (IV*) and nonradioactive 2-fluoro-3-hydroxybenzylacrylate (IV) on a Supelco Discovery C18 HPLC column equipped with UV (A1) and NaI γ-ray (A2) detectors. B, Elution spectrum of (±)-[$^{18}$F]-3-fluoro-2-hydroxypropionate (V*) on a Nucleosil C18 Pyramid HPLC column equipped with a NaI γ-ray detector.

The present invention is further illustrated by the following examples.

I. Chemical Examples

I.1. Material and Methods

Chemicals.

[$^{18}$O]—H$_2$O was from Rotem. Benzyl acrylate was from Alpha Aesar; DMSO and tetrabutylammonium bicarbonate (TBAHCO$_3$) from ABX; H$_3$PO$_4$ from Riedel-de Hain; Kryptofix 2.2.2. from Merck; NaH$_2$PO$_4$ and HPLC acetonitrile from VWR; and CDCl$_3$ and TMS from Euristop. All other reagents were from Sigma-Aldrich.

High-Performance Liquid Chromatography (HPLC).

HPLC was performed on Gilson equipment (305 and 302 pumps) equipped with UV/VIS-151 and γ-ray NaI detectors connected in series and monitored by a GABI Star interface module (Raytest). Columns were for semi-preparative HPLC: Dionex Supelco Discovery C18, 5 µm, 250×10 mm; for analytical HPLC: MN, 150/4.6 Nucleosil 100-5 C18, 150 mm, ID: 4.6 mm and IonPac AS15, Dionex.

Production of [$^{18}$F]-Fluoride.

[$^{18}$F]-fluoride was produced on a medical-isotope cyclotron (IBA Cyclone 18/9) using a [$^{18}$O]—H$_2$O liquid target. After irradiation, the target water was passed through a Chromafix 30-PS-HCO$_3$ (Macherey-Nagel) or Accel Plus QMA Sep Pak light cartridge (Waters) to trap the [$^{18}$F]-fluoride.

General Scheme of Synthesis:

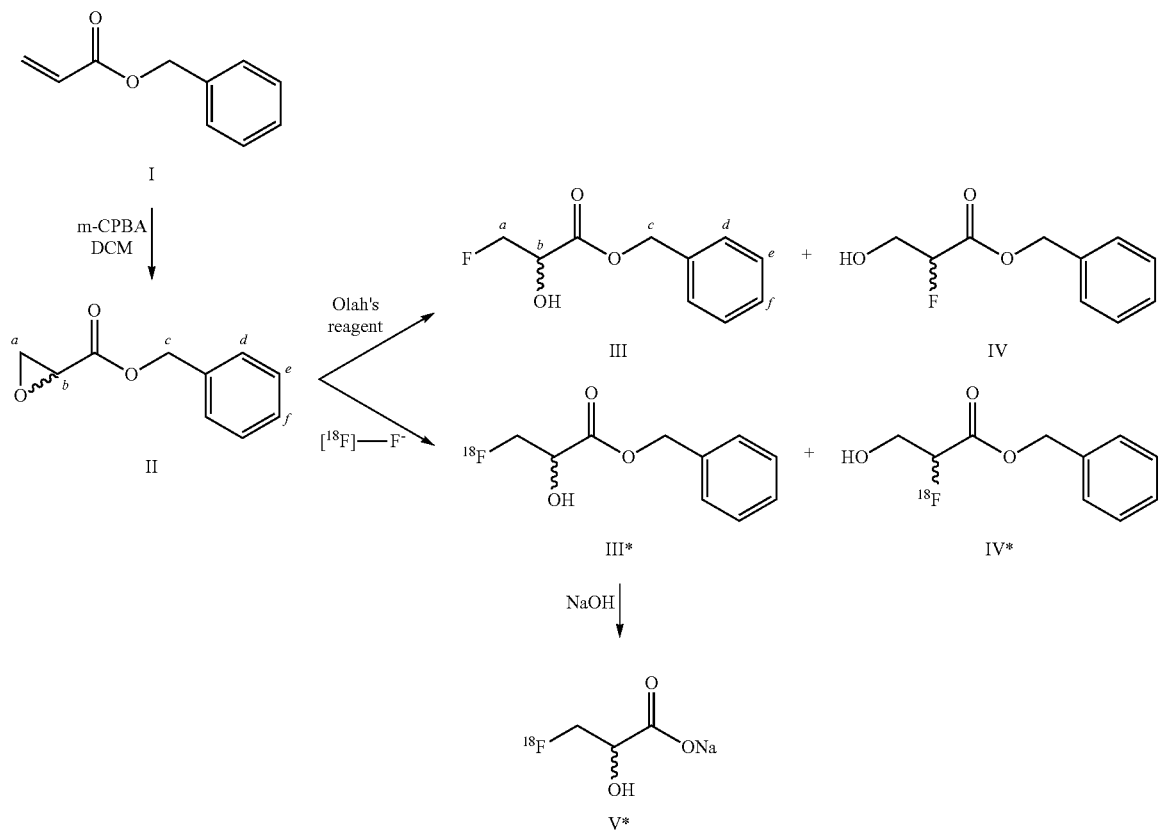

I.2. Synthesis of benzyl oxirane-2-carboxylate (II)

3-Chloroperoxybenzoic acid (14.04 g) was added to a solution of benzyl acrylate (I) (23.04 mmol in 90 mL of dry dichloromethane (DCM)). The reaction mixture was heated under reflux and stirring for 7 days. DCM (100 mL) was then added to the solution, and washed twice with a saturated aqueous solution of sodium carbonate. The remaining DCM fraction was concentrated to 30 mL (rotavapor vacuum), and ethyl acetate (150 mL) was added. This solution was again washed twice with a saturated aqueous solution of sodium carbonate, and the recombined organics layers were dried over sodium sulfate, filtered and concentrated to dryness under reduced pressure. The crude was finally purified by silica gel chromatography using cyclohexane/ethyl acetate (95/5, 100 mL; and 10/90, 800 mL), and remaining volatiles were removed under vacuum to yield the desired compound (II). Yield: 53%, $^1$H NMR (CDCl$_3$ with 0.03% v/v TMS, 400 MHz): δ 7.38 (5.29H, m, $H_d$, $H_e$ and $H_f$), 5.18-5.27 (2.7H, q, $H_c$), 3.47-3.49 (1H, dd, $H_b$), 2.94-3.01 (2.18H, qd, $H_a$).

I.3. Synthesis of (±)-[$^{18}$F]-3-fluoro-2-hydroxypropionate (V*)

Method I.

A Chromafix 30-PS-HCO$_3$ cartridge loaded with [$^{18}$F]-fluoride was eluted in reverse order to a reaction vessel using a solution of 0.075 M of tetrabutylammonium bicarbonate (TBAHCO$_3$, 80 µL, 6 µmol) in acetonitrile (0.9 mL). Anhydrous [$^{18}$F]-fluoride was obtained by azeotropic distillation with acetonitrile at 95° C. under a stream of helium. [$^{18}$F]-fluoride recovery was of more than 80%. Benzyl oxirane-2-carboxylate (II) (10 µL) dissolved in anhydrous DMSO (1 mL) was added to the [$^{18}$F]-fluoride and was reacted for 10 minutes at 120° C. After cooling, the reaction mixture was diluted by 3.5 mL water and passed through a neutral alumina cartridge (Waters) to discard unreacted [$^{18}$F]-fluoride. It yield 2 regioisomers: (±)-[$^{18}$F]-benzyl 3-fluoro-2-hydroxypropionate (III*) and (±)-[$^{18}$F] benzyl 2-fluoro-3-hydroxypropionate (IV*). About 90% of the [$^{18}$F] radioactivity incorporated in organic molecules was related to both regioisomers (III*) and (IV*), with an about 1/1 ratio (FIG. 1A2).

Figure 2:
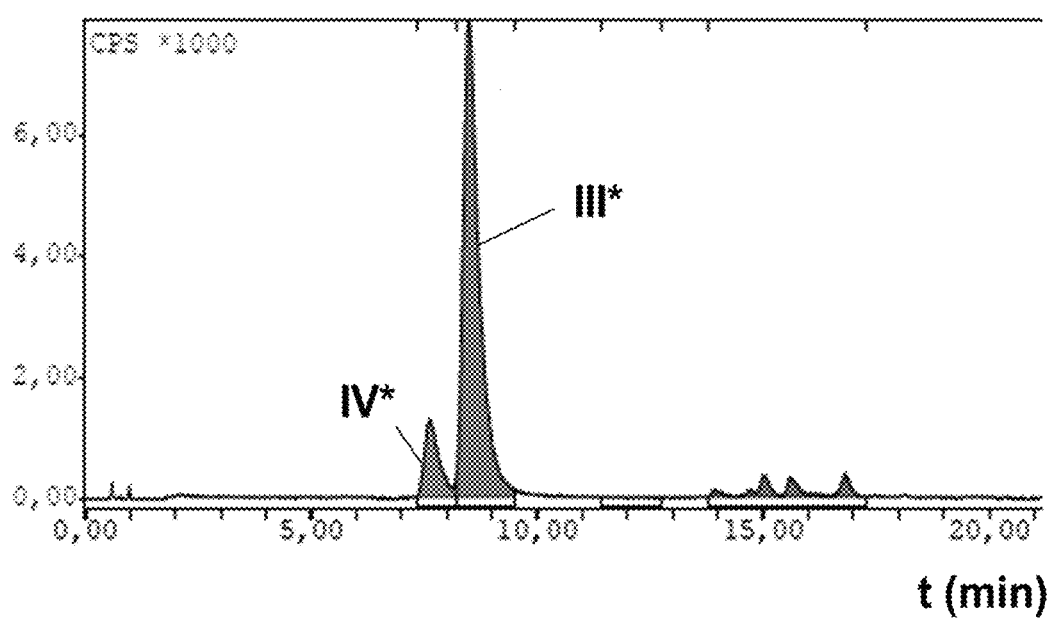
FIG. 2. Elution spectrum of (±)-[$^{18}$F]-benzyl 3-fluoro-2-hydroxypropionate (III*) and (±)-[$^{18}$F]-2-fluoro-3-hydroxybenzylacrylate (IV*) on a Supelco Discovery C18 HPLC column equipped with a NaI γ-ray detector, showing regioisomer ratio when tert-amyl alcohol was used as a fluorination solvent (Method II).

Compounds (III*) and (IV*) (NaI detector) co-eluted with nonradioactive benzyl 3-fluoro-2-hydroxypropionate (III) and benzyl 2-fluoro-3-hydroxypropionate (IV) (UV detector), respectively (FIGS. 1A2 and 1A1).

The (±)-[$^{18}$F]-benzyl 3-fluoro-2-hydroxypropionate (III*) was isolated by semi-preparative HPLC (20 mM NaH$_2$PO$_4$/CH$_3$CN 70/30, 3 mL/min, retention time=21 min), diluted with water (1.5×vol), and loaded on a conditioned C18 Sep-Pak cartridge (Waters). The cartridge was rinsed with 10 mL of water and then loaded with 0.5 N NaOH. After 5 minutes, (±)-[$^{18}$F]-3-fluoro-2-hydroxypropionate (III*) was eluted with 1 mL of water, and pH set to 7.0 by the addition of H$_3$PO$_4$. (±)-[$^{18}$F]-3-fluoro-2-hydroxypropionate (V*) was characterized by analytical HPLC (IonPac AS15, Dionex, 14 mM of NaOH as eluent), with a retention time of 5.25 min (FIG. 1B).

Method II.

A Chromafix 30-PS-HCO$_3$ cartridge loaded with [$^{18}$F]-fluoride was eluted in reverse order to a reaction vessel using a 30 µL aqueous solution of 0.55 mg K$_2$C$_2$O$_4$ (3.0 µmol)/2.25 mg Kryptofix 2.2.2. (6.0 µmol) diluted in 1 mL of "Trace Select" methanol. Anhydrous [$^{18}$F]-fluoride was obtained by azeotropic distillation with acetonitrile at 95° C. under a stream of helium. Benzyl oxirane-2-carboxylate (II) (10 µL) dissolved in anhydrous 2-methyl-2-butanol (1 mL) was added to the [$^{18}$F]-fluoride. The vial was sealed and heated at 105° C. for 10 minutes. Solvent was then evaporated to dryness at 100° C. under a stream of helium. After cooling, the reaction mixture was diluted by 4.5 mL of an acetonitrile/water 1/2 solution, and passed through a neutral alumina cartridge to discard unreacted [$^{18}$F]-fluoride. (±)-[$^{18}$F]-3-fluoro-2-hydroxypropionate (V*) was then prepared as in Method I.

In method II, by conducting the radiofluorination reaction in 2-methyl-2-butanol, a protic solvent, the regioselectivity of the epoxide opening improved up to more than 80% for (±)-[$^{18}$F]-benzyl 3-fluoro-2-hydroxypropionate (III*) (FIG. 2), and the global fluorination yield slightly increased (15-20%).

I.4. Synthesis of Reference Compound benzyl 3-fluoro-2-hydroxypropionate (III)

To a solution of benzyl oxirane-2-carboxylate (II) (1.12 g) in dry DCM (7.5 mL) cooled to 0° C. was added Olah's reagent (Hydrogen fluoride pyridine: pyridine~30%, hydrogen fluoride~70%, 3.4 mL) dropwise. After reaching room temperature, the mixture was stirred for 35 h. The biphasic solution was added on a silica suspension in DCM (100 ml), then filtered and washed with 50 mL of DCM. The desired benzyl 3-fluoro-2-hydroxypropionate (III) was further purified over silica gel chromatography. $^1$H NMR (CDCl$_3$ with 0.03% v/v TMS, 400 MHz): δ 7.35-7.39 (5.29H, m, $H_d$, $H_e$ and $H_f$), 5.28 (1.85H, s, $H_c$), 4.59-4.76 (1.94H, dqd, $H_a$), 4.35-4.44 (0.92H, dquint, $H_b$). The undesired regioisomer benzyl 2-fluoro-3-hydroxypropionate (IV) was obtained under the form of traces (FIG. 1A1).

II. Biological Examples

Statistics.

Data were analyzed using GraphPad Prism version 6.04 for Windows. All results are expressed as mean±SEM. N refers to the number of independent experiments and n to the total number of replicates per treatment condition. Error bars are sometimes smaller than symbols. Student's t test and one-way ANOVA was used where appropriate. $P<0.05$ was considered to be statistically significant.

II.1. Lactate Dehydrogenase Assay

A potential reduction of 3-fluoropyruvate to 3-fluoro-2-hydroxypropionate by lactate dehydrogenase (LDH) was measured in vitro using a previously reported protocol (Goncalves et al., Tetrahedron: Asymmetry, 1996, 7, 1237-1240).

Briefly, 14.6 mg of nonradioactive 3-fluorpyruvate were dissolved in 4 mL of double distilled water containing 10 IU of rabbit muscle LDH (Sigma) and 5.3 IU of formate dehydrogenase (Sigma). The reaction was started by adding NADH to a final concentration of 0.2 mM and sodium formate to a final concentration of 40 mM. The final volume was adjusted to 5 mL with double distilled water. The reaction was carried out at 37° C. for 24 h under constant, gentle shaking at 120 rpm. Then, solution was spun through a 10 kDa filter to remove enzymes, and 3-fluoro-2-hydroxypropionate was detected by HPLC-MS using an Accela U(HPLC) equipped with a Luna Phenomenex 250*4.60 HPLC column and an ThermoScientific LTQ-ORBITRAP-XL fitted an electrospray ionization source working in negative mode.

Figure 3:
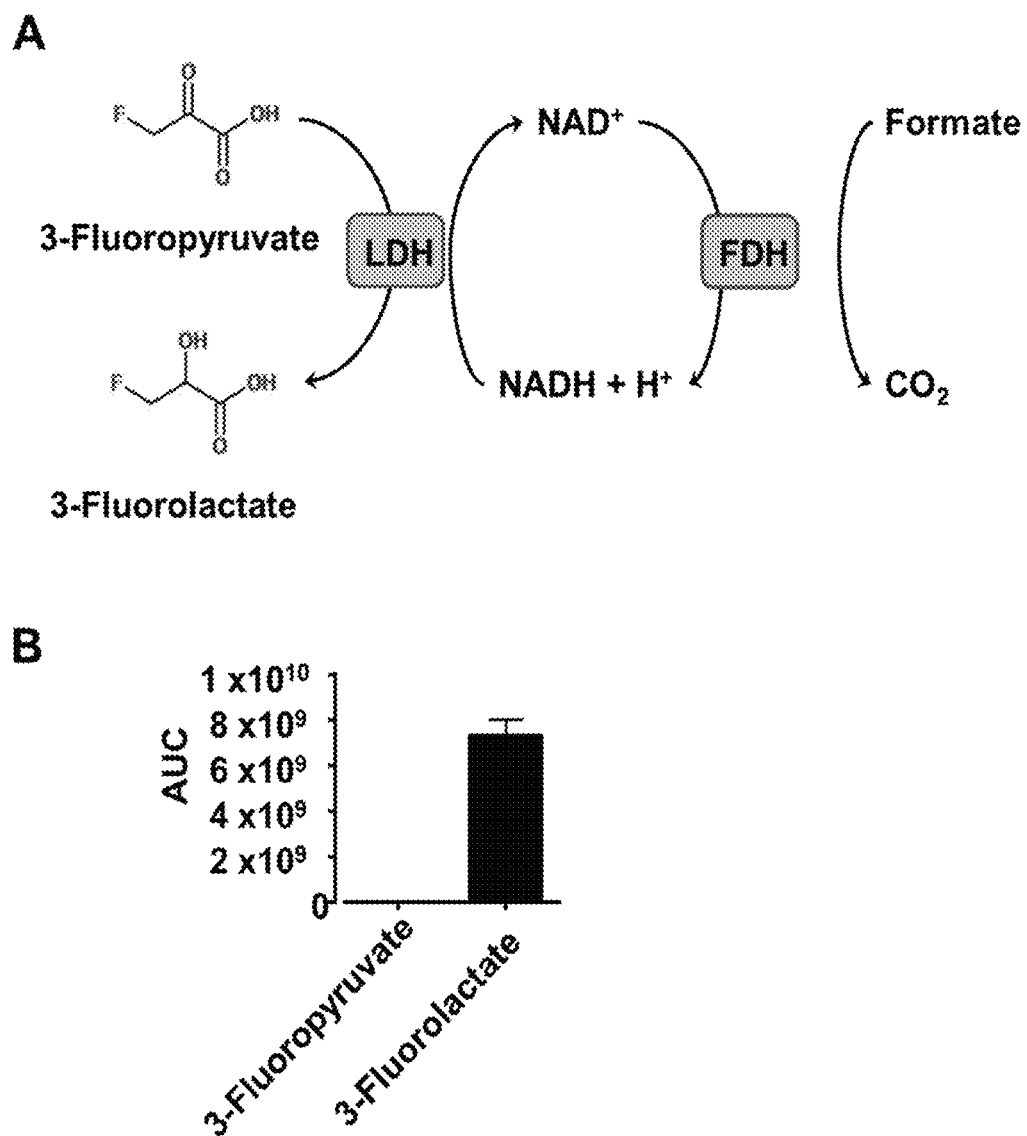
FIG. 3. 3-fluoropyruvate can be reduced to 3-fluoralacate by lactate dehydrogenase (LDH). A, Scheme of the reaction used for 3-fluoropyruvate reduction. B, 3-fluorpyruvate and 3-fluoralacate detection using mass spectrometry after the reaction schematized in A (n=3; N=1).

Data of FIG. 3 support the possibility that (±)-[$^{18}$F]-3-fluorolactate could be metabolized to [$^{18}$F]-3-fluoropyruvate by LDH, i.e., along the oxidative pathway of lactate in oxidative cancer cells.

II.2. Oxidative Cancer Cells Take Up and Trap (±)-[$^{18}$F]-3-fluoro-2-hydroxypropionate In Vitro Cells and Gene Silencing.

HeLa and SiHa human cervix squamous cell carcinoma and SDQ9 human laryngeal squamous cell carcinoma were from ATCC. Cells were routinely cultured in DMEM (Thermo Fischer) containing glucose (4.5 g/L), Glutamax and 10% FBS. MCT1-deficient and control SiHa cells were produced as previously described (De Saedeleer et al., Oncogene, 2014, 33, 4060-4068), using the following vectors from Open Biosystems: TRCN0000038340 (shMCT1-1) and TRCN0000038339 (shMCT1-2). Control shRNA (shCTR) was Addgene plasmid 1864.

Western Blotting.

Western blotting was performed as previously described (Van Hée et al., Front Pharmacol, 2015, 6, 228). Primary antibodies were a rabbits polyclonals against MCT1 (Merck Millipore # AB3538P) and MCT4 (Corbet C et al., Cancer Res, 2014, 74, 5507-5519); and mouse monoclonals against Hsp90 (BD Bioscience #610419), CD147 (BD Bioscience #555961) and β-Actin (Sigma # A5441).

Oximetry.

Basal oxygen consumption rates were determined on a Seahorse XF96 bioenergetic analyzer according to manufacturer's recommendations. Twenty thousand cells per well were plated 18-h before the experiment in DMEM without glucose and glutamine, containing 10% dialyzed FBS, and L-lactate (10 mM), ±D-glucose (25 mM). Data are normalized to cell number at the end of the experiment.

In Vitro Tracer Uptake Assay.

A modified version of the $^{14}$C-Lactate uptake assay described by Draoui et al., (Draoui et al., Bioorg Med Chem, 2013, 21, 7107-7117) was used. Briefly, 250,000 cells were plated in flat-bottom 24 well plates (t=0). When cells were attached (t=6 h), medium was replaced by DMEM without glucose and glutamine, containing 10% dialyzed FBS and 10 mM of L-lactate, pH 7.0. Cells were then incubated overnight at 37° C., 5% $CO_2$. On the day of experiment, (t=24 h), cells medium was removed and cells were briefly washed twice with a modified KREBS solution without glucose (HEPES 25 mM, NaCl 120 mM, KCl 4.8 mM, $KH_2PO_4$ 1.2 mM, $MgSO_4$ 1.2 mM, $CaCl_2$ 2 mM). Where indicated, the cells were treated during 12 min with α-cyano-4-hydroxycinnamte (CHC, 30 µM), AR-C155858 (10 µM) or vehicle in KREBS containing 10 mM of L-lactate. After incubation, the solution was replaced by the KREBS solution containing 10 mM of L-Lactate, pharmacological agents or vehicle and [$^{18}$F]-3-fluoro-2-hydroxypropionate (45 µCi/ml). Cells were incubated for 10 min for (±)-[$^{18}$F]-3-fluoro-2-hydroxypropionate, after which the solution was removed and the cells were washed 3 times with an ice-cold KREBS solution containing L-Lactate (10 mM). Cells were lysed with NaOH 0.1 N, and $^{18}$F activity was measured in the cell lysate using a Wiper Gold γ-counter (Laboratory Technologies). Activity is expressed as % of initial dose. For background determination, wells without cells were treated in the exact same way.

Results.

Figure 4:
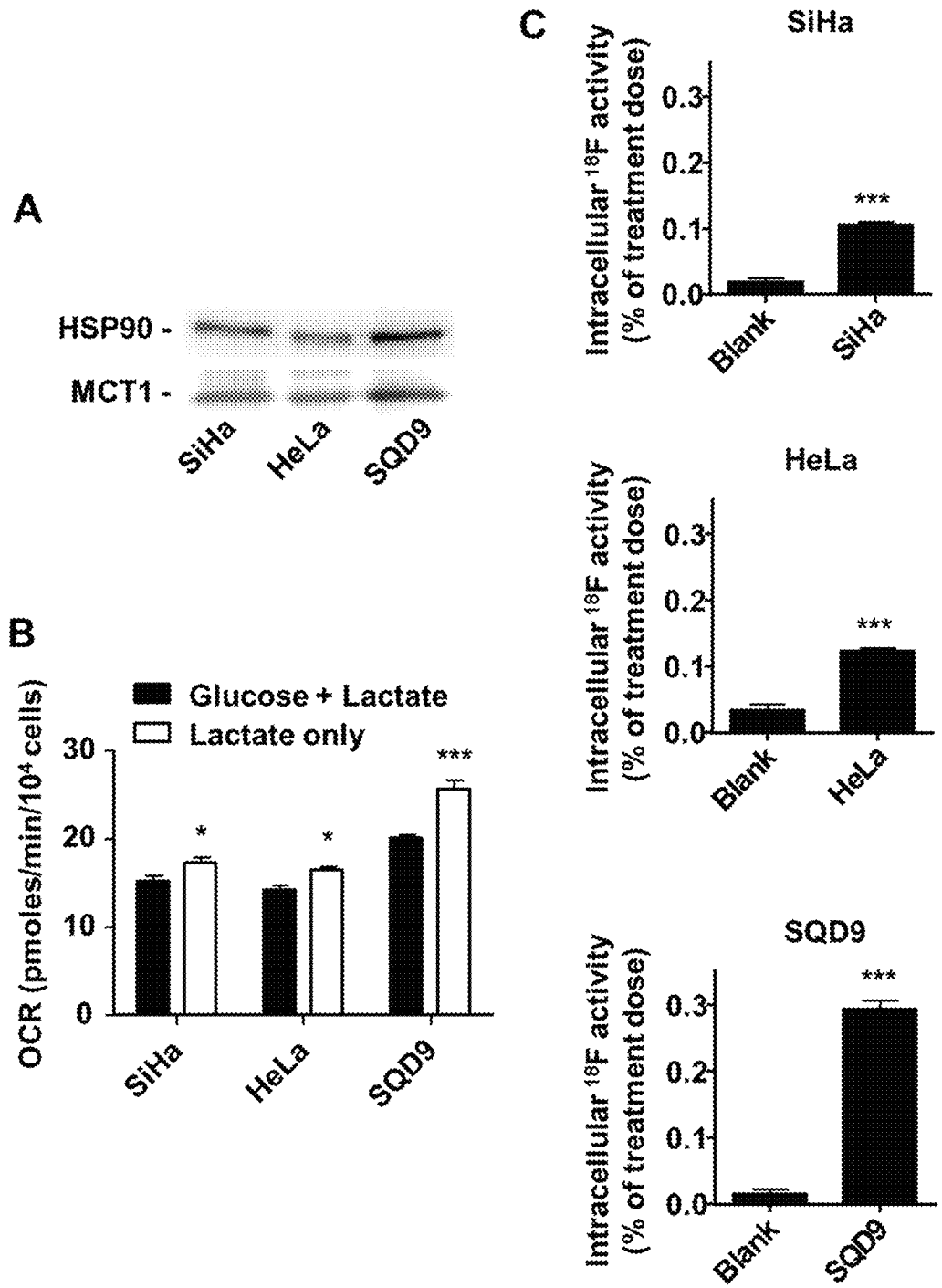
FIG. 4. Oxidative human cancer cells trap (±)-[$^{18}$F]-3-fluoro-2-hydroxypropionate (V*). A, Representative western blots showing MCT1 expression in SiHa, HeLa and SQD9 human cancer cells. B, The oxygen consumption rate (OCR) of SiHa, HeLa and SQD9 cells on a Seahorse bioanalyzer. Cells received either glucose (25 mM)+L-lactate (10 mM) or only L-lactate (10 mM) as oxidative fuels in DMEM containing 10% of dialyzed FBS (n=8, *P<0.05, ***P<0.005). C, Cancer cells (or empty wells; blanks) were incubated during 6 min in the presence of (±)-[$^{18}$F]-3-fluoro-2-hydroxypropionate (V*) (45 µCi/ml), washed, and intracellular $^{18}$F activity was measured using a Wiper Gold γ-counter (n=12-14, N=2, ***P<0.001).

To evaluate (±)-[$^{18}$F]-3-fluoro-2-hydroxypropionate as a potential tracer of lactate uptake by oxidative cancer cells, SiHa, HeLa and SDQ9 cells were selected for in vitro assays. Indeed, all 3 cell lines did express MCT1 (FIG. 4A), and oximetry on a Seahorse bioanalyzer confirmed that HeLa and SQD9 were at least as oxidative as SiHa cells in vitro (FIG. 4B). As previously reported for SiHa (Sonveaux et al., J Clin Invest, 2008, 118, 3930-3942), the cells could use lactate as an oxidative fuel in the absence of glucose (FIG. 4B). In vitro, they took up and trapped (±)-[$^{18}$F]-3-fluoro-2-hydroxypropionate 6 min after the delivery of 45 µCi/ml of the tracer (FIG. 4C). At this time, intracellular doses ranged from ~0.1% for SiHa and HeLa to ~0.3% of the initial dose for SQD9. It was thus considered that (±)-[$^{18}$F]-3-fluoro-2-hydroxypropionate can qualify as a tracer of lactate uptake by oxidative cancer cells.

II.3. Validation of (±)-[$^{18}$F]-3-fluoro-2-hydroxypropionate as a Tracer of Lactate Uptake by Tumors In Vivo In Vivo Tracer Uptake Assay.

All in vivo experiments were performed with approval of UCL Comité d'Ethique pour l'Experimentation Animale (approval ID 2014/UCL/MD/014) according to national and European animal care regulations. To avoid inter-subject variability, 500,000 SiHa-shCTR and SiHa-shMCT1 cells in a HBSS:Matrigel 1:1 solution were respectively injected in the left and right flank of same 6.5 week-old male NMRI nude mice. In another model, 1,000,000 SQD9 cells in a HBSS:Matrigel 1:1 solution were injected on the back of same 6.5 week-old male NMRI nude mice. Experiments were performed on tumors of ~10 mm in diameter, i.e., about 3 weeks tumor cell inoculation. For intravenous injection, MCT1 inhibitor AR-C155858 (Tocris) was dissolved in 0.9% NaCl with 10% (2-hydroxypropyl)-β-cyclodextrin at a concentration of 2.5 mg/ml (Vijay et al., Pharm Res, 2015, 32, 1894-1906). For intravenous injection, MCT1 inhibitor AZD3965 (Selleckchem) was first dissolved in pure ethanol at a concentration of 100 mg/ml, then diluted in 0.9% NaCl with 10% (2-hydroxypropyl)-β-cyclodextrin at a final concentration of 2.5 mg/ml. (±)-[$^{18}$F]-3-fluoro-2-hydroxypropionate (150-250 µCi) was injected in the tail vein of the animals 10 min after the delivery of AR-C155858 (5 mg/Kg), AZD3965 (5 mg/Kg), or vehicle (70 µL). At indicated times, a whole body 10-min static PET imaging (small-animal Mosaic PET Scan system, Philips Medical Systems) directly followed by a 10 min transmission CT scan (NanoSPECT/CT Small Animal Imager, Bioscan; source: 370 MBq $^{137}$Cs; X-Ray tube voltage: 55 kVp; number of projections: 180; exposure time 1000 ms) were performed on isoflurane-anesthetized mice kept at 35° C. PET images were corrected for attenuation and reconstructed using fully 3D iterative algorithm 3D-RAMLA in a 128×128×120 matrix, with a voxel size of 1 mm$^3$. CT images were reconstructed with a voxel size of 0.221× 0.221×0.221 mm$^3$. 2D Regions of interest (ROIs) were manually delineated on PET images using the PMOD software version 3.5 (PMOD technologies Ltd). Tumor localization was determined on PET/CT fused images. Ribcage and skin were used as internal and external limits, respectively. Tracer uptake is expressed as standard uptake value (SUV) calculated on the mean value of voxels within the manually defined 3D volume of interest (VOI).

Results.

Figure 5:
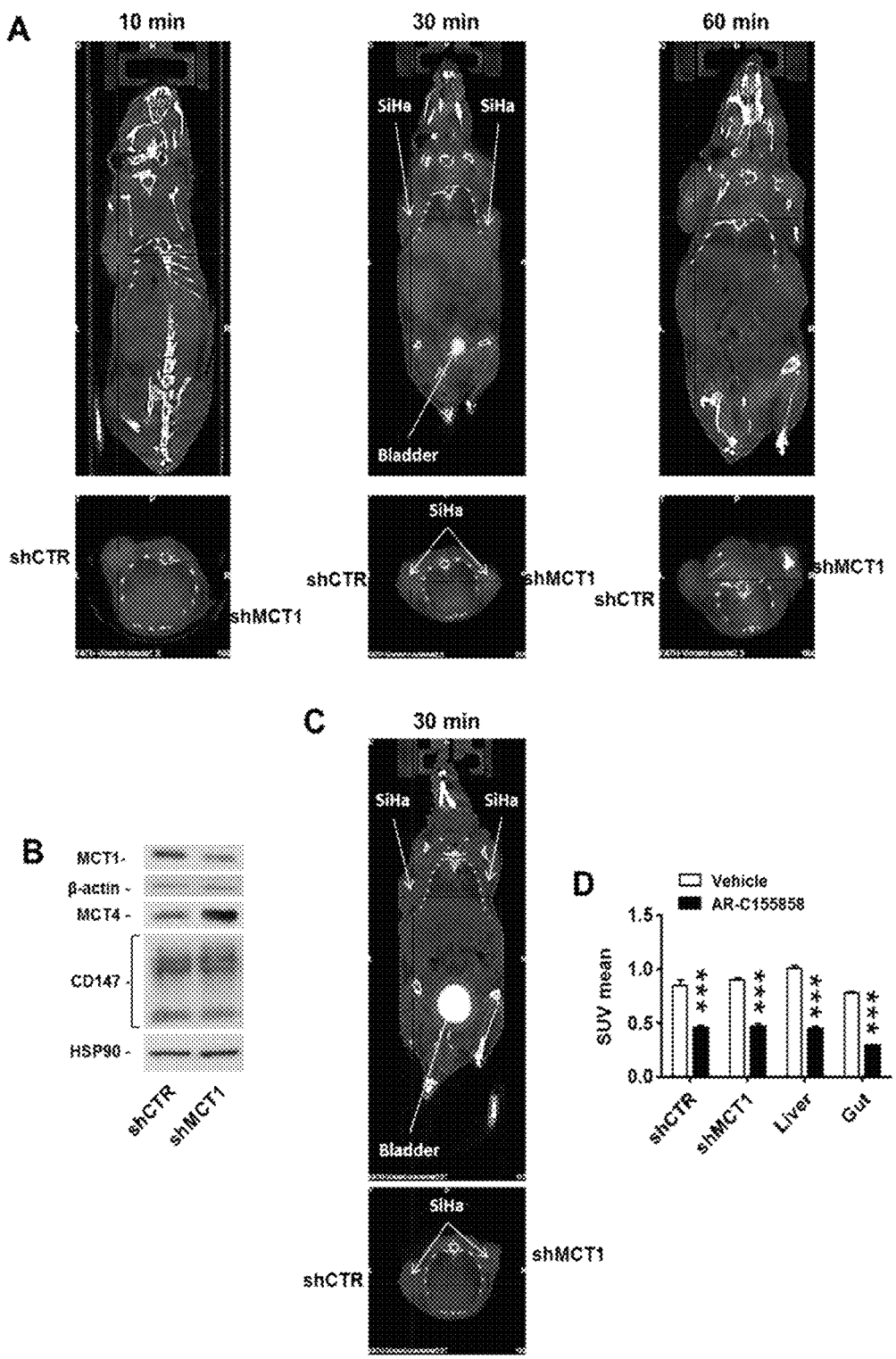
FIG. 5. MCT1 inhibitor AR-C155858 blocks the in vivo uptake of (±)-[$^{18}$F]-3-fluoro-2-hydroxypropionate (V*) by SiHa tumors in mice. Mice were bearing 2 SiHa tumors expressing a control shRNA (shCTR) or a shRNA against MCT1 (shMCT1). A, Representative images of vehicle-pretreated mice showing the physiological distribution of (±)-[$^{18}$F]-3-fluoro-2-hydroxypropionate (V*) 10, 30 and 60 min after tail vein injection (215 µCi in 100 µL). Color scale is normalized for the injected dose and animal weight. B, Western blot showing MCT1, MCT4, β-actin and Hsp90 expression in SiHa cells infected with shCTR or shMCT1 (Representative of n=3). C, Same as in A, except that mice were pretreated with AR-C155858 (5 mg/Kg IV 10 min before tracer injection). The representative image shows the exact same mouse as in A (30 min tracer image), assessed the day after. The bladder is indicated. D, Quantification of A and C (n=6-7; N=2, ***P<0.001).

To validate (±)-[$^{18}$F]-3-fluoro-2-hydroxypropionate as a tracer of lactate uptake by tumors, mice bearing 2 SiHa tumors that expressed either shCTR or shMCT1 were used. This model is the original model in which the metabolic symbiosis based on lactate exchange was demonstrated (Sonveaux et al., J Clin Invest, 2008, 118, 3930-3942). (±)-[$^{18}$F]-3-fluoro-2-hydroxypropionate was administered IV at a dose of 150-250 µCi. PET/CT images revealed that tracer distribution was time-dependent, with best tumor contrast 30 min after tracer injection (FIG. 5A). Other organs known to express MCTs and to take up lactate, such as the gut and the liver, were also labeled. At this time point, there was no detectable bone labeling that could have indicated defluorination. Of note, 60 min after tracer injection, spinal and joint labeling was detected, indicating that some defluorination had occurred (FIG. 5A). At 30 min, there was no apparent discrimination of SiHa-shCTR and SiHa-shMCT1 by the tracer. This lack of difference was explained by a compensatory overexpression of MCT4 upon MCT1 silencing, which was detected by western blotting (FIG. 5B).

It was therefore decided to evaluate the ability of (±)-[$^{18}$F]-3-fluoro-2-hydroxypropionate to detect a pharmacological inhibition of MCT1, thus recapitulating at best a clinical treatment. One day after the initial determination of tracer biodistribution, the same group of mice was treated with MCT1 inhibitor AR-C155858 (5 mg/Kg) administered IV 10 min before a second PET/CT scan. Images acquired 30 min after (±)-[$^{18}$F]-3-fluoro-2-hydroxypropionate delivery revealed that MCT1 inhibition by AR-C155858 induced a highly significant decrease in tracer uptake in the tumors, liver and gut (FIGS. 5C&D). The bladder, which was already apparent on pre-treatment images (FIG. 5A, 30 min), was much more positively marked after systemic MCT1 inhibition (FIG. 5C), indicating that urine is the preferred route for (±)-[$^{18}$F]-3-fluoro-2-hydroxypropionate clearance. Accordingly, kidneys, that preferentially express MCT2 for lactate clearance, were labelled after treatment. Note that for comparison, PET/CT scans of the same mouse is shown in FIGS. 5A&C at the 30 min acquisition time, with a color scale normalized for the injected dose.

Figure 6:
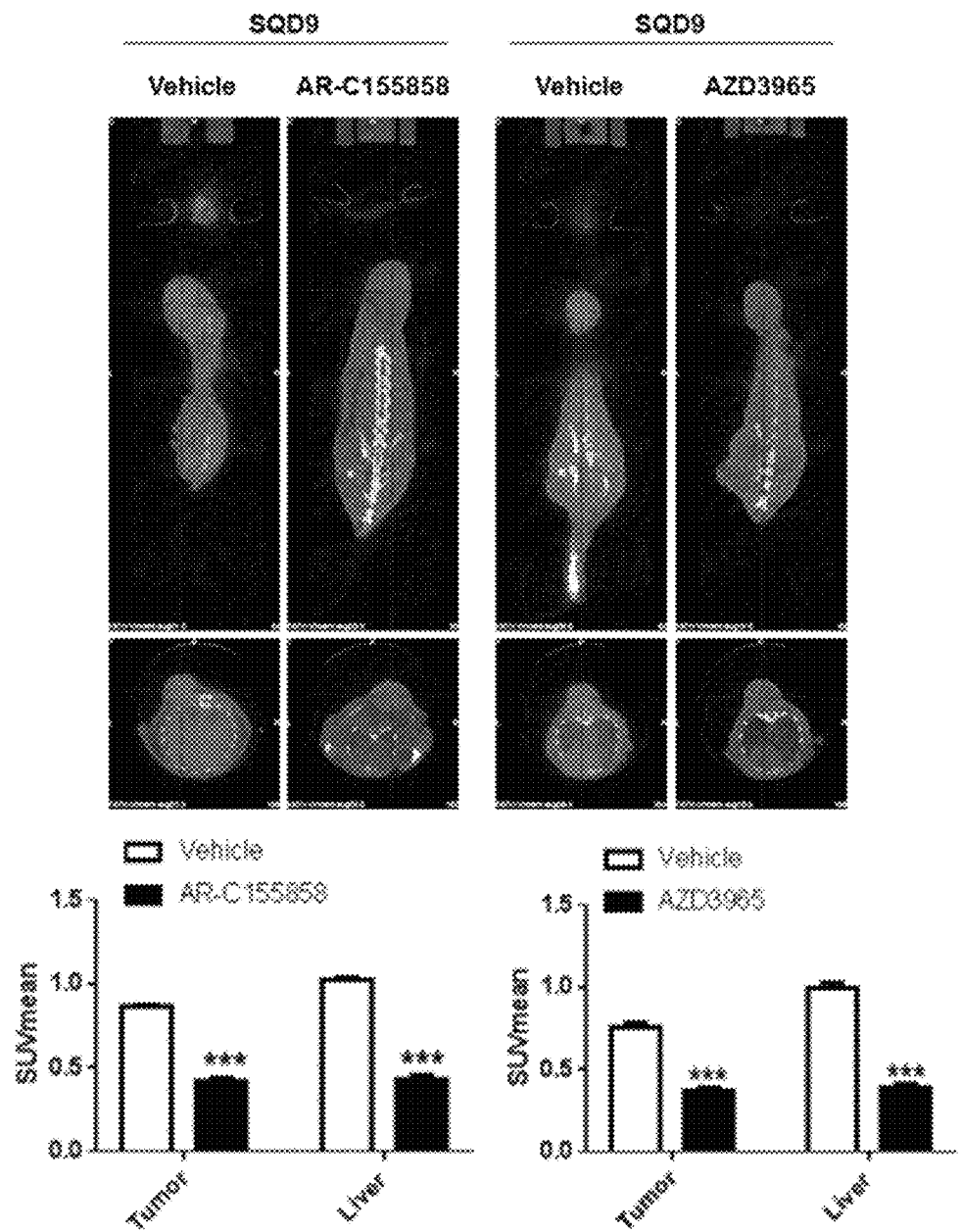
FIG. 6. (±)-[$^{18}$F]-3-fluoro-2-hydroxypropionate allows to document an early response of SQD9 head and neck cancer to MCT1 inhibitors AR-C155858 and AZD3965. MCT1 inhibitors AR-C155858 or AZD3965 were injected intravenously at a dose of 5 mg/kg. (±)-[$^{18}$F]-3-fluoro-2-hydroxypropionate (250 µCi) was injected intravenously 10 minutes after injection. Images were acquired 30 minutes after tracer injection. Arrows indicate SQD9 tumor localization (n=6). ***P<0.005 compared to vehicle, using Student's t test.

To confirm the ability of (±)-[$^{18}$F]-3-fluoro-2-hydroxypropionate to detect a pharmacological inhibition of MCT1, the experiment was repeated using SQD9 human laryngeal squamous cell carcinoma cells in mice. (±)-[$^{18}$F]-3-fluoro-2-hydroxypropionate was administered IV at a dose of 250 µCi to the tumor-bearing mice, and PET-CT images were acquired showing that the tumors captured and accumulated the tracer. On the next day using the same mice, MCT1 inhibitor AR-C155858 (5 mg/Kg) or AZD3965 (5 mg/Kg) were administered IV 10 min before a second PET/CT scan. Images acquired 30 min after (±)-[$^{18}$F]-3-fluoro-2-hydroxypropionate delivery revealed that MCT1 inhibition by AR-C155858 or, alternatively, AZD3965 induced a highly significant decrease in tracer uptake in the tumors and liver (FIG. 6).

The invention claimed is:

1. A compound which is [18F]-3-fluoro-2-hydroxypropionic acid:

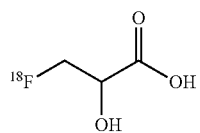

or a pharmaceutically acceptable salt and/or solvate thereof.

2. The compound according to claim 1, wherein the salt is [$^{18}$F]-3-fluoro-2-hydroxypropionate sodium salt.

3. A pharmaceutical composition comprising the compound according to claim 1, and at least one pharmaceutically acceptable excipient.

4. A medicament comprising the compound according to claim 1.

5. A method for predicting and/or monitoring if a tumor of an individual displays a therapeutic response to a treatment for modulating lactate uptake and/or lactate metabolism, comprising
    (1) when the method is a method for monitoring, administering to an individual a treatment for modulating lactate uptake and/or lactate metabolism;
    (2) administering to said individual an amount of the compound according to claim 1, sufficient to be detected by PET;
    (3) forming at least one PET image of the tumor; and
    (4) determining the lactate uptake of the tumor by observing the image.

6. The method according to claim 5, wherein the treatment for modulating lactate uptake is selected from drugs that inhibit monocarboxylate transporters.

7. The method according to claim 5, wherein the treatment for modulating lactate metabolism is selected from drugs that inhibit lactate dehydrogenase.

8. A method for in vitro detection of lactate uptake in a tissue, said method comprising
    (1) contacting said tissue with an amount of the compound according to claim 1, sufficient to be detected by PET;
    (2) forming at least one PET image; and
    (3) determining lactate uptake by observing the image.

9. A method for imaging cancer cells, said method comprising
    (1) administering to an individual with cancer an amount of the compound according to claim 1 sufficient to be detected by PET; and
    (2) forming at least one PET image showing the distribution of said compound, within the cancer cells of the individual.

10. A method for monitoring a cancer therapy in an individual, said method comprising
    (1) administering a cancer therapy to an individual;
    (2) administering to said individual an amount of the compound according to claim 1, sufficient to achieve imaging; and
    (3) performing imaging using PET by detecting a signal from said compound, within the individual, to follow the response of the individual to the therapy.

11. A process of manufacturing of [$^{18}$F]-3-fluoro-2-hydroxypropionic acid or a pharmaceutically acceptable salt and/or solvate thereof, comprising the following steps:
    a) an epoxide-ring opening reaction on benzyl oxirane-2-carboxylate (II)

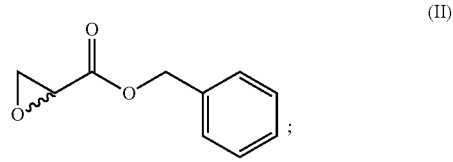 [SMILES: O=C(OCc1ccccc1)C1CO1]

in presence of [$^{18}$F]-fluoride, to afford [$^{18}$F]-benzyl 3-fluoro-2-hydroxypropionate (III*)

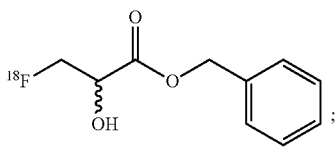

(III*)

and b) hydrolysis of [$^{18}$F]-benzyl 3-fluoro-2-hydroxypropionate (III*) to afford [$^{18}$F]-3-fluoro-2-hydroxypropionic acid or a pharmaceutically acceptable salt and/or solvate thereof.

12. The process according to claim 11, comprising a preliminary step of synthesis of benzyl oxirane-2-carboxylate (II) by epoxidation of benzyl acrylate.

13. The method according to claim 6, wherein the drug that inhibits monocarboxylate transporters is a drug that inhibits monocarboxylate transporter 1.

14. The method according to claim 7, wherein the drugs that inhibit lactate dehydrogenase are selected from drugs that inhibit lactate dehydrogenase B, mitochondrial pyruvate carrier or alanine transaminase.

15. A method to detect lactate uptake in a cell or a population of cells, said method comprising:
(1) administering to a cell or a population of cells an amount of the compound according to claim 1 sufficient to be detected by PET;
(2) forming at least one PET image showing the distribution of said compound within the cell or the population of cells; and
(3) determining lactate uptake by observing the image.

* * * * *